(12) United States Patent
Bronkalla

(10) Patent No.: US 10,607,735 B2
(45) Date of Patent: Mar. 31, 2020

(54) HYBRID RENDERING SYSTEM FOR MEDICAL IMAGING APPLICATIONS

(71) Applicant: INTERNATIONAL BUSINESS MACHINES CORPORATION, Armonk, NY (US)

(72) Inventor: Mark Bronkalla, Hartland, WI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/257,579

(22) Filed: Sep. 6, 2016

(65) Prior Publication Data

US 2018/0068065 A1  Mar. 8, 2018

(51) Int. Cl.
| | |
|---|---|
| *G16H 40/63* | (2018.01) |
| *G06T 19/00* | (2011.01) |
| *G16H 30/40* | (2018.01) |
| *G16H 10/60* | (2018.01) |
| *G16H 15/00* | (2018.01) |

(52) U.S. Cl.
CPC ............ *G16H 40/63* (2018.01); *G06T 19/00* (2013.01); *G16H 10/60* (2018.01); *G16H 15/00* (2018.01); *G16H 30/40* (2018.01); *G06T 2210/41* (2013.01)

(58) Field of Classification Search
None
See application file for complete search history.

(56) References Cited

U.S. PATENT DOCUMENTS

| | | | |
|---|---|---|---|
| 6,608,628 B1 | 8/2003 | Ross et al. | |
| 6,711,297 B1 | 3/2004 | Chang et al. | |
| 7,859,549 B2 * | 12/2010 | Handley | H04N 1/0035 345/619 |
| 10,056,012 B2 | 8/2018 | Geri et al. | |
| 2008/0140722 A1 | 6/2008 | Jakobovits | |
| 2009/0129643 A1 * | 5/2009 | Natanzon | G06F 19/321 382/128 |
| 2011/0255763 A1 | 10/2011 | Bogoni et al. | |
| 2013/0166767 A1 * | 6/2013 | Olivier | H04L 65/60 709/231 |
| 2017/0200270 A1 * | 7/2017 | Reicher | G06F 19/321 |
| 2018/0225862 A1 | 8/2018 | Petkov | |

OTHER PUBLICATIONS

Kagadis et a ("Medical Imaging Displays and Their Use in Image Interpretation", 2013, RadioGraphics) (Year: 2013).*

* cited by examiner

*Primary Examiner* — Xin Sheng
(74) *Attorney, Agent, or Firm* — Erik Huestis; Stephen Kenny; Foley Hoag

(57) ABSTRACT

Hybrid rendering systems for medical imaging applications are provided. In some embodiments, an indication of a viewing mode is received at a medical image viewer from a user. The viewing mode is a diagnostic mode or a referential mode. A plurality of characteristics of the medical image viewer are determined. Based upon the viewing mode and the plurality of characteristics of the medical image viewer, a rendering mode is determined. The rendering mode is a server-side rendering mode or a client-side rendering mode. A request for medical imagery is sent. The request conforms to the rendering mode. The medical imagery is rendered according to the rendering mode. The requested medical imagery is displayed on the medical image viewer.

20 Claims, 4 Drawing Sheets

HYBRID RENDERING SYSTEM FOR MEDICAL IMAGING APPLICATIONS

BACKGROUND

Embodiments of the present invention relate to medical imagery rendering, and more specifically, to a hybrid rendering system for medical imaging applications.

BRIEF SUMMARY

According to embodiments of the present disclosure, a method of and computer program product for hybrid rendering are provided. An indication of a viewing mode is received at a medical image viewer from a user. The viewing mode is a diagnostic mode or a referential mode. A plurality of characteristics of the medical image viewer are determined. Based upon the viewing mode and the plurality of characteristics of the medical image viewer, a rendering mode is determined. The rendering mode is a server-side rendering mode or a client-side rendering mode. A request for medical imagery is sent. The request conforms to the rendering mode. The medical imagery is rendered according to the rendering mode. The requested medical imagery is displayed on the medical image viewer.

DETAILED DESCRIPTION

A Picture Archiving and Communication System (PACS) is a medical imaging system that provides storage and access to images from multiple modalities. In many healthcare environments, electronic images and reports are transmitted digitally via PACS, thus eliminating the need to manually file, retrieve, or transport film jackets. A standard format for PACS image storage and transfer is DICOM (Digital Imaging and Communications in Medicine). Non-image data, such as scanned documents, may be incorporated using various standard formats such as PDF (Portable Document Format) encapsulated in DICOM.

Most viewing systems operate either as client side, or server side rendering systems.

Client side systems generally download images to a PACS Client, then decompress and perform rendering operations (e.g., window/level, pan/zoom). Annotations are applied, 3D operations are performed (e.g., MIP, MPR, Color volume rendering), or fusion is performed on the client device. The client device is typically a PC. This has the advantage of generally being very fast and responsive once the images are present on the client device. The disadvantage is that the entire set of images needs to be transferred to the client even though the user will not actually look at all of them (particularly for 3D operations). This becomes problematic for large data sets and slow network connections (e.g., home or remote users). Client side rendering may be required when there is a need for fast lossless display of groups of images at high quality (e.g., cardiac catheterization studies or breast tomosynthesis) where the user wants to scroll through or cine play at speeds of 20-60 frames per second at aggregate resolutions of 3-12 Megapixels. Such a rate outstrips most available network speeds, especially for remote users.

Server side rendering systems perform these rendering operations on the image processing server and then provide a rendered version of the image to the viewing client. The rendered image may be transferred in lossy or losslessly formats, and this may change during manipulations or in the case of slow connections. This technique may be referred to as streaming. An example in which server side rendering is advantageous is the cardiac CT. In this case, there may be 7000 or more slice images that are only viewed as a 3D rendering requiring only a few hundred image renders to be displayed to the client user.

In light of the drawbacks of an exclusively client-side or exclusively server-side rendering solution, there is a need for a hybrid solution so that an individual study can be handled on the client or server side and to provide a mixed mode. In some embodiments, a rule based approach is adopted, in which various user and study parameters such as the slice thickness, number of slices, image resolution, or study size are used to determine whether to client or server side render.

Figure 1:
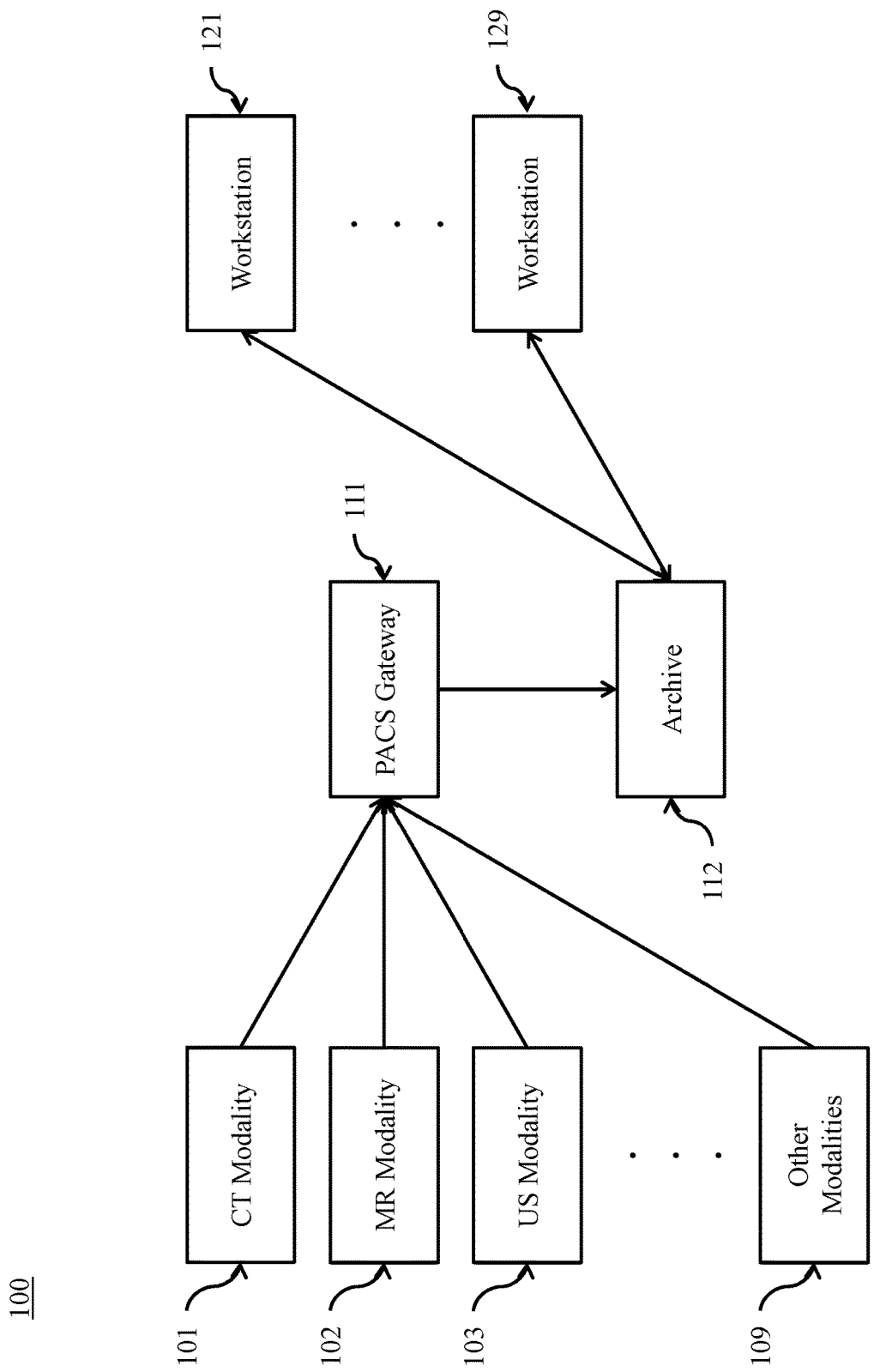
FIG. 1 depicts an exemplary Picture Archiving and Communication System.

Referring to FIG. 1, an exemplary PACS 100 consists of four major components. Various imaging modalities 101 . . . 109 such as computed tomography (CT) 101, magnetic resonance imaging (MRI) 102, or ultrasound (US) 103 provide imagery to the system. In some implementations, imagery is transmitted to a PACS Gateway 111, before being stored in archive 112. Archive 112 provides for the storage and retrieval of images and reports. Workstations 121 . . . 129 provide for interpreting and reviewing images in archive 112. In some embodiments, a secured network is used for the transmission of patient information between the components of the system. In some embodiments, workstations 121 . . . 129 may be web-based viewers. PACS delivers timely and efficient access to images, interpretations, and related data, eliminating the drawbacks of traditional film-based image retrieval, distribution, and display.

A PACS may handle images from various medical imaging instruments, such as X-ray plain film (PF), ultrasound (US), magnetic resonance (MR), Nuclear Medicine imaging, positron emission tomography (PET), computed tomography (CT), endoscopy (ES), mammograms (MG), digital radiography (DR), computed radiography (CR), Histopathology, or ophthalmology. However, a PACS is not limited to a predetermined list of images, and supports clinical areas beyond conventional sources of imaging such as radiology, cardiology, oncology, or gastroenterology.

Different users may have a different view into the overall PACS system. For example, while a radiologist may typically access a viewing station, a technologist may typically access a QA workstation.

In some implementations, the PACS Gateway 111 comprises a quality assurance (QA) workstation. The QA workstation provides a checkpoint to make sure patient demographics are correct as well as other important attributes of a study. If the study information is correct the images are passed to the archive 112 for storage. The central storage device, archive 112, stores images and in some implementations, reports, measurements and other information that resides with the images.

Once images are stored to archive 112, they may be accessed from reading workstations 121 . . . 129. The reading workstation is where a radiologist reviews the patient's study and formulates their diagnosis. In some implementations, a reporting package is tied to the reading workstation to assist the radiologist with dictating a final report. A variety of reporting systems may be integrated with the PACS, including those that rely upon traditional dictation. In some implementations, CD or DVD authoring software is included in workstations 121 . . . 129 to burn patient studies for distribution to patients or referring physicians.

In some implementations, a PACS includes web-based interfaces for workstations 121 . . . 129. Such web interfaces may be accessed via the internet or a Wide Area Network (WAN). In some implementations, connection security is provided by a VPN (Virtual Private Network) or SSL (Secure Sockets Layer). The clients side software may comprise ActiveX, JavaScript, or a Java Applet. PACS clients may also be full applications which utilize the full resources of the computer they are executing on outside of the web environment.

Communication within PACS is generally provided via Digital Imaging and Communications in Medicine (DICOM). DICOM provides a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format.

DICOM groups information into data sets. For example, a file containing a particular image, generally contains a patient ID within the file, so that the image can never be separated from this information by mistake. A DICOM data object consists of a number of attributes, including items such as name and patient ID, as well as a special attribute containing the image pixel data. Thus, the main object has no header as such, but instead comprises a list of attributes, including the pixel data. A DICOM object containing pixel data may correspond to a single image, or may contain multiple frames, allowing storage of cine loops or other multi-frame data. DICOM supports three- or four-dimensional data encapsulated in a single DICOM object. Pixel data may be compressed using a variety of standards, including JPEG, Lossless JPEG, JPEG 2000, and Run-length encoding (RLE). LZW (zip) compression may be used for the whole data set or just the pixel data.

Figure 2:
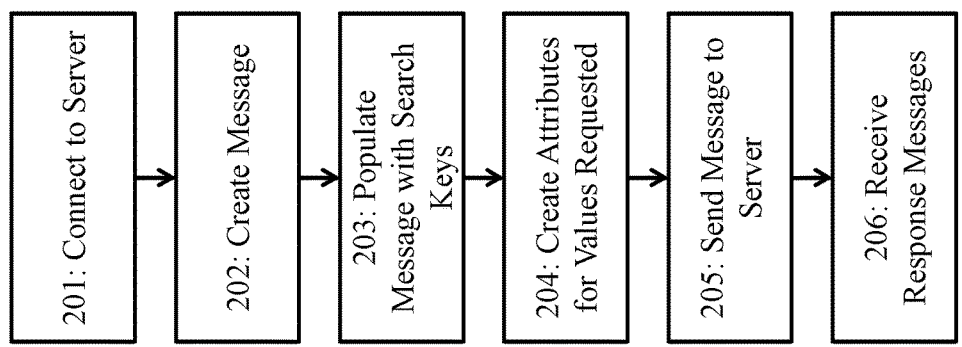
FIG. 2 illustrates an exemplary clinical image search and retrieval method.

Referring to FIG. 2, an exemplary PACS image search and retrieval method 200 is depicted. Communication with a PACS server, such as archive 112, is done through DICOM messages that that contain attributes tailored to each request. At 201, a client, such as workstation 121, establishes a network connection to a PACS server. At 202, the client prepares a DICOM message, which may be a C-FIND, C-MOVE, C-GET, or C-STORE request. At 203, the client fills in the DICOM message with the keys that should be matched. For example, to search by patient ID, a patient ID attribute is included. At 204, the client creates empty attributes for all the values that are being requested from the server. For example, if the client is requesting an image ID suitable for future retrieval of an image, it include an empty attribute for an image ID in the message. At 205, the client send the message to the server. At 206, the server sends back to the client a list of one or more response messages, each of which includes a list of DICOM attributes, populated with values for each match.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

According to various embodiments of the present disclosure, a rules-based system for determining rendering methodology is provided. In some embodiments, the rules are based on the user, their role, and their current activity (e.g., actively reading vs. purely referential viewing). In some circumstances, diagnostic reading may have restrictions placed on the user or system. For example, some sites may require that the base study be read at lossless or original image quality yet allow lossy reproduction for priors. Similarly, there may be legal mandates such as MQSA that require mammography studies to be read at original, lossless image quality. An individual user may switch between primary reading and referential viewing roles depending on a variety of external factors (e.g., conference presentation, reading shift, or night or remote consultation).

In some embodiments, the rules are based on study type. For example, cardiac CT will may be preferentially server-side rendered. Mammographic tomosynthesis may be client side rendered for diagnostic reading, due to MQSA regulations and to accommodate the ability to scroll through 2-4 datasets at 20 fps each with resolutions of 3-6 MP per image. However, referential review may generally be server side, irrespective of the restrictions imposed on primary reading modes. Similarly, server side rendering may be required for quality of service when on mobile devices. Cardiology viewing may be preferentially client side due to high aggregate frame rates, but may vary between client and server side depending on the rules.

In some embodiments, the rules are based on the client device in use at the time. For example, different policies may apply to desktop PCs, Macs, tablets, or mobile phones. In particular, certain mobile devices may be unsuitable for client-side rendering of large volumes due to memory limitations and available bandwidth.

In some embodiments, the rules are based on available bandwidth and latency to the client at viewing time. In high-latency networks, operations may preferentially be performed at the client-side for many study types due to the network's negative impact on interactivity. For example, where the user is in a different city than the server, latency may be in the 100 ms range. With this amount of latency, there can be no more than 10 interactions per second (before taking into account the actual transfer time for the rendered images).

It is not desirable to always render and upsample (interpolated) to the final display resolution on the server. Particularly in cases where the display is very high resolution (e.g., >8 MP). Accordingly, in some embodiments, images are transferred at their original resolution or at an intermediate resolution (as for 3D renderings). In such cases, final interpolation is performed on the client.

Figure 3:
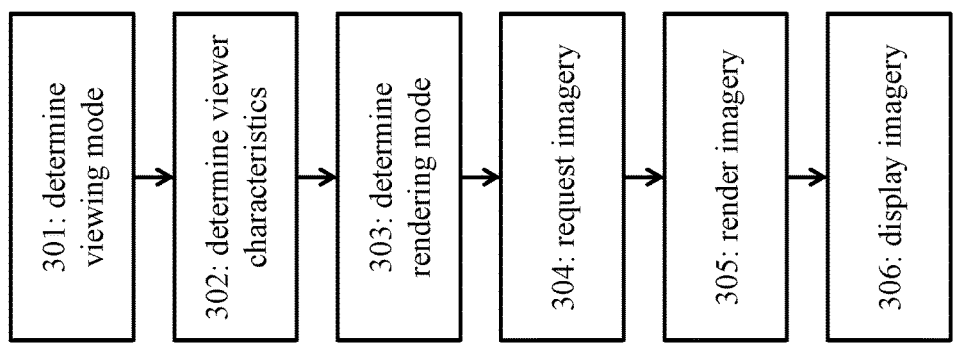
FIG. 3 illustrates an exemplary method of hybrid rendering according to embodiments of the present disclosure.

Referring now to FIG. 3, a method 300 for hybrid rendering according to embodiments of the present disclosure is illustrated. At 301, an indication of a viewing mode is received at a medical image viewer from a user. In some embodiments, the viewing mode is a diagnostic mode or a referential mode. At 302, a plurality of characteristics of the medical image viewer are determined. Based upon the viewing mode and the plurality of characteristics of the medical image viewer, a rendering mode is determined at 303. In some embodiments, the rendering mode is a server-side rendering mode or a client-side rendering mode. At 304, a request for medical imagery is sent. The request conforms to the rendering mode. At 305, the medical imagery is rendered according to the rendering mode. In some embodiments, rendering is performed on the client side, while in some embodiments it is performed on the server. At 306, the requested medical imagery is displayed on the medical image viewer.

Figure 4:
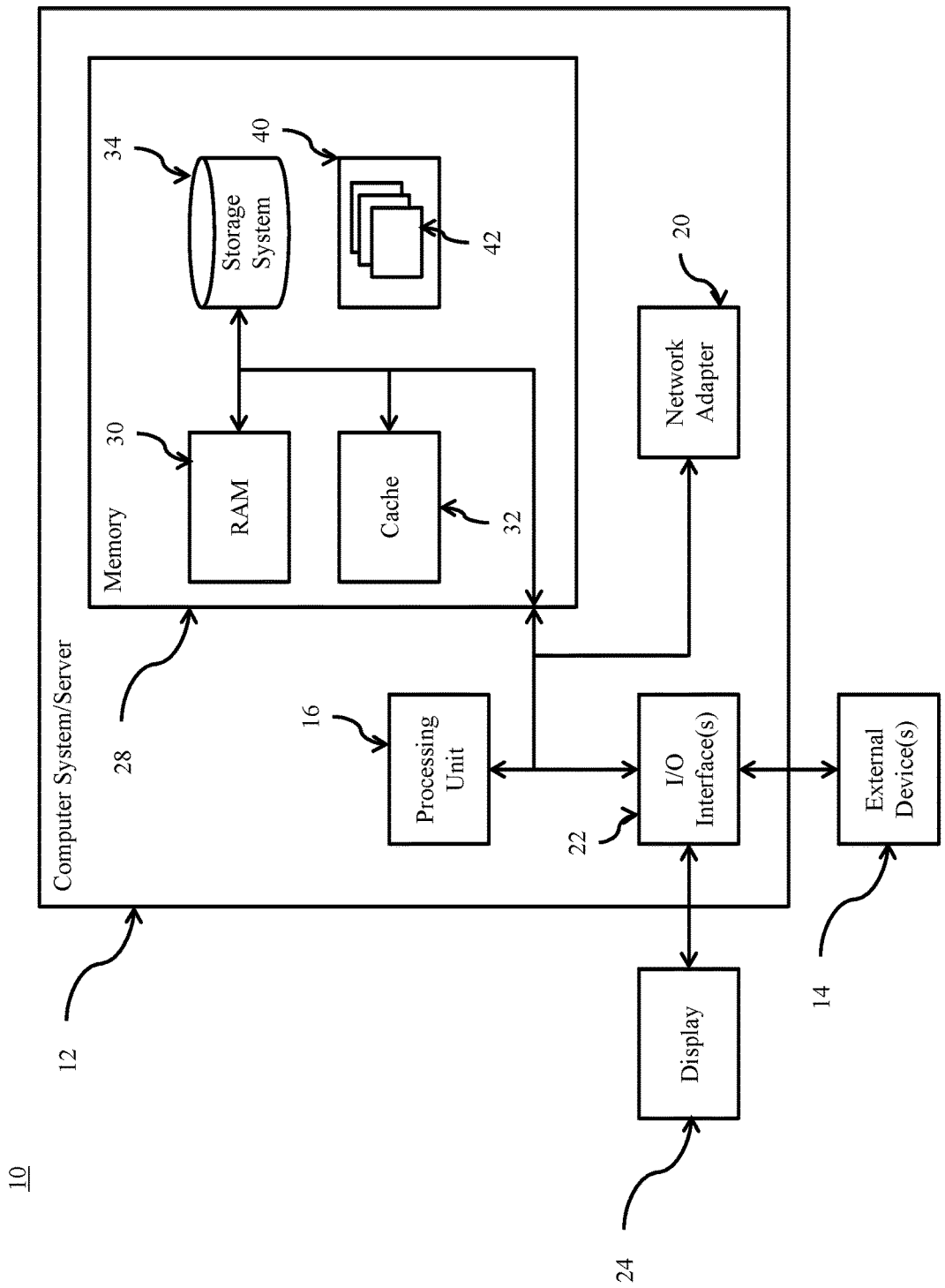
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   receiving at a medical image viewer an indication from a user of a viewing mode, the viewing mode being a diagnostic mode or a referential mode;
   determining a plurality of characteristics of the medical image viewer;
   determining a restriction imposed on diagnostic reading of a study comprising medical imagery having at least one medical image, the restriction comprising an image resolution requirement;
   determining a rendering mode based upon the viewing mode, the restriction, and the plurality of characteristics of the medical image viewer, wherein determining the rendering mode comprises:
      when the viewing mode is indicated as the diagnostic mode, selecting a client-side rendering mode and indicating lossless reproduction for each of the at least one medical image, the client-side rendering mode having a first frame rate, wherein rendering is performed at the medical image viewer;
      when the viewing mode is indicated as the referential mode, selecting a server-side rendering mode and indicating lossy reproduction for each of the at least one medical image, the server-side rendering mode having a second frame rate that is higher than the first frame rate, wherein rendering is performed at a server;
   sending a request to the server for the medical imagery, the request conforming to the rendering mode;
   rendering the medical imagery according to the rendering mode; and
   displaying the requested medical imagery on the medical image viewer.

2. The method of claim 1, wherein determining the rendering mode comprises applying a plurality of rendering rules.

3. The method of claim 2, wherein the plurality of rendering rules are associated with the medical imagery.

4. The method of claim 3, wherein the association is based on a study including the medical imagery.

5. The method of claim 3, wherein the association is based on a series including the medical imagery.

6. The method of claim 1, further comprising:
   receiving at the medical image viewer an indication from the user to change the viewing mode; and
   determining a second rendering mode based on the change in viewing mode.

7. The method of claim 6, further comprising:
   downloading medical imagery for client-side rendering.

8. The method of claim 1, wherein the plurality of characteristics of the medical image viewer comprises a user role, a device profile of the medical image viewer, a network connection speed between the medical image viewer and a medical imagery provider, a study type associated with the medical imagery, user preferences associated with a user of the medical image viewer, site level restrictions imposed on the medical image viewer, a minimum quality requirement for the medical imagery, a minimum resolution requirement for the medical imagery, a requirement for lossless compression, and a study size associated with the medical imagery.

9. The method of claim 1, further comprising upsampling the requested medical imagery at the image viewer.

10. A computer program product for hybrid rendering, the computer program product comprising a computer readable storage medium having program instructions embodied therewith, the program instructions executable by a processor to cause the processor to perform a method comprising:
   receiving at a medical image viewer an indication from a user of a viewing mode, the viewing mode being a diagnostic mode or a referential mode;
   determining a plurality of characteristics of the medical image viewer;
   determining a restriction imposed on diagnostic reading of a study comprising medical imagery having at least one medical image, the restriction comprising an image resolution requirement;
   determining a rendering mode based upon the viewing mode, the restriction, and the plurality of characteristics of the medical image viewer, wherein determining the rendering mode comprises:
      when the viewing mode is indicated as the diagnostic mode, selecting a client-side rendering mode and indicating lossless reproduction for each of the at least one medical image, the client-side rendering mode having a first frame rate, wherein rendering is performed at the medical image viewer;
      when the viewing mode is indicated as the referential mode, selecting a server-side rendering mode and indicating lossy reproduction for each of the at least one medical image, the server-side rendering mode having a second frame rate that is higher than the first frame rate, wherein rendering is performed at a server;
   sending a request to the server for the medical imagery, the request conforming to the rendering mode;
   rendering the medical imagery according to the rendering mode; and
   displaying the requested medical imagery on the medical image viewer.

11. The computer program product of claim 10, wherein determining the rendering mode comprises applying a plurality of rendering rules.

12. The computer program product of claim 11, wherein the plurality of rendering rules are associated with the medical imagery.

13. The computer program product of claim 12, wherein the association is based on a study including the medical imagery.

14. The computer program product of claim 12, wherein the association is based on a series including the medical imagery.

15. The computer program product of claim 10, the method further comprising:
   receiving at the medical image viewer an indication from the user to change the viewing mode; and
   determining a second rendering mode based on the change in viewing mode.

16. The computer program product of claim 15, the method further comprising:
   downloading medical imagery for client-side rendering.

17. The computer program product of claim 10, wherein the plurality of characteristics of the medical image viewer comprises a user role, a device profile of the medical image viewer, a network connection speed between the medical image viewer and a medical imagery provider, a study type associated with the medical imagery, user preferences associated with a user of the medical image viewer, site level restrictions imposed on the medical image viewer, a minimum quality requirement for the medical imagery, a minimum resolution requirement for the medical imagery, a requirement for lossless compression, and a study size associated with the medical imagery.

18. The computer program product of claim 10, further comprising upsampling the requested medical imagery at the image viewer.

19. A system for viewing medical images comprising:
   a repository of medical images;
   a client-side image renderer;
   a server-side image renderer;
   a display for viewing medical images from the repository;
   at least one computer readable storage medium having program instructions embodied therewith, the program instructions executable by a processor to:
   receive an indication from a user of a viewing mode, the viewing mode being a diagnostic mode or a referential mode;
   determine a plurality of characteristics of a medical image viewer;
   determine a restriction imposed on diagnostic reading of a study comprising medical imagery having at least one medical image, the restriction comprising an image resolution requirement;
   determine a rendering mode based upon the viewing mode, the restriction, and the plurality of characteristics of the medical image viewer, wherein determining the rendering mode comprises:
      when the viewing mode is indicated as the diagnostic mode, selecting a client-side rendering mode and indicating lossless reproduction for each of the at least one medical image, the client-side rendering mode having a first frame rate, wherein rendering is performed at the medical image viewer;
      when the viewing mode is indicated as the referential mode, selecting a server-side rendering mode and indicating lossy reproduction for each of the at least one medical image, the server-side rendering mode having a second frame rate that is higher than the first frame rate, wherein rendering is performed at a server;
   send a request to the server for the medical imagery, the request conforming to the rendering mode;
   render the medical imagery according to the rendering mode; and
   display the requested medical imagery on the medical image viewer.

20. The system of claim 19, the program instructions further executable by a processor to:
   receiving at the medical image viewer an indication from the user to change the viewing mode; and
   determining a second rendering mode based on the change in viewing mode.

* * * * *